United States Patent
Chevallier et al.

(10) Patent No.: US 9,220,848 B2
(45) Date of Patent: Dec. 29, 2015

(54) SYRINGE DEVICE COMPRISING A SYRINGE BODY AND A BEARING SLEEVE

(75) Inventors: Stephane Chevallier, Saint-Soupplets (FR); Jean-Michel Chevallier, Enghien-les-Bains (FR)

(73) Assignee: Tech Group Europe Limited, Dublin (IE)

( * ) Notice: Subject to any disclaimer, the term of this patent is extended or adjusted under 35 U.S.C. 154(b) by 13 days.

(21) Appl. No.: 12/738,509

(22) PCT Filed: Oct. 22, 2008

(86) PCT No.: PCT/FR2008/051908
§ 371 (c)(1),
(2), (4) Date: Apr. 16, 2010

(87) PCT Pub. No.: WO2009/056735
PCT Pub. Date: May 7, 2009

(65) Prior Publication Data
US 2010/0217205 A1    Aug. 26, 2010

(30) Foreign Application Priority Data
Oct. 23, 2007 (FR) ..................................... 07 58497

(51) Int. Cl.
*A61M 5/31* (2006.01)
*A61M 5/32* (2006.01)

(52) U.S. Cl.
CPC ............. *A61M 5/326* (2013.01); *A61M 5/3129* (2013.01); *A61M 5/3135* (2013.01); *A61M 2005/3238* (2013.01); *A61M 2005/3261* (2013.01)

(58) Field of Classification Search
CPC ...................... A61M 5/326; A61M 2005/3247; A61M 5/3137; A61M 5/3234; A61M 5/3243; A61M 2005/3139; A61M 5/3257; A61M 5/3271; A61M 2005/3264; A61M 5/3135; A61M 5/3245; A61M 2005/3261; A61M 5/3275

USPC .................................................. 604/110, 198
See application file for complete search history.

(56) References Cited

U.S. PATENT DOCUMENTS

| 1,921,034 A | 8/1933 | La Marche |
| 3,880,163 A | 4/1975 | Ritterskamp |

(Continued)

FOREIGN PATENT DOCUMENTS

| EP | 0904792 A2 | 3/1999 |
| EP | 0966983 A1 | 12/1999 |

(Continued)

OTHER PUBLICATIONS

Int'l Preliminary Report on Patentability issued Jun. 1, 2010 in Int'l Application No. PCT/FR2008/051907.

(Continued)

*Primary Examiner* — Bhisma Mehta
*Assistant Examiner* — Laura Schell
(74) *Attorney, Agent, or Firm* — Panitch Schwarze Belisario & Nadel LLP

(57) ABSTRACT

The invention relates to a device comprising a syringe body (10) having an axial direction (A) and a bearing sleeve (18) inside which the body is arranged. The sleeve has at least one holding lug (22) co-operating with the syringe body, at a proximal end (10A) of the latter, in order to hold the body in relation to the sleeve. Said proximal end is fixed to a wedging surface (42) having radial crenulations forming dips (42B) and bumps (42A) and the holding lug is inserted into a dip in order to prevent a relative rotation of the syringe body (10) and the sleeve perpendicularly to the axial direction.

11 Claims, 3 Drawing Sheets

(56) References Cited

U.S. PATENT DOCUMENTS

| | | | |
|---|---|---|---|
| 4,631,057 A * | 12/1986 | Mitchell | 604/198 |
| 4,723,943 A | 2/1988 | Spencer | |
| 4,747,831 A | 5/1988 | Kulli | |
| 4,828,548 A | 5/1989 | Walter | |
| 4,832,696 A | 5/1989 | Luther et al. | |
| 4,871,355 A | 10/1989 | Kikkawa | |
| 4,887,998 A | 12/1989 | Martin et al. | |
| 4,911,693 A | 3/1990 | Paris | |
| 4,923,447 A | 5/1990 | Morgan | |
| 4,927,416 A | 5/1990 | Tomkiel | |
| 4,929,237 A | 5/1990 | Medway | |
| 4,931,040 A | 6/1990 | Haber et al. | |
| 4,943,282 A | 7/1990 | Page et al. | |
| 4,966,592 A | 10/1990 | Burns et al. | |
| 4,986,819 A | 1/1991 | Sobel | |
| 5,026,349 A | 6/1991 | Schmitz et al. | |
| 5,106,379 A | 4/1992 | Leap | |
| 5,108,378 A | 4/1992 | Firth et al. | |
| 5,112,307 A | 5/1992 | Haber et al. | |
| 5,141,500 A | 8/1992 | Hake | |
| 5,163,918 A * | 11/1992 | Righi et al. | 604/198 |
| 5,201,708 A | 4/1993 | Martin | |
| 5,201,720 A | 4/1993 | Borgia et al. | |
| 5,261,880 A | 11/1993 | Streck et al. | |
| 5,267,972 A | 12/1993 | Anderson | |
| 5,279,581 A | 1/1994 | Firth et al. | |
| 5,346,480 A | 9/1994 | Hess et al. | |
| 5,360,410 A | 11/1994 | Wacks | |
| 5,380,296 A | 1/1995 | Smedley et al. | |
| 5,411,487 A | 5/1995 | Castagna | |
| 5,501,672 A | 3/1996 | Firth et al. | |
| 5,531,706 A | 7/1996 | de la Fuente | |
| 5,558,651 A | 9/1996 | Crawford et al. | |
| 5,573,513 A | 11/1996 | Wozencroft | |
| 5,591,138 A | 1/1997 | Vaillancourt | |
| 5,601,536 A | 2/1997 | Crawford et al. | |
| 5,803,918 A | 9/1998 | Vetter et al. | |
| 5,817,064 A | 10/1998 | DeMarco et al. | |
| 5,855,839 A | 1/1999 | Brunel | |
| 5,891,104 A | 4/1999 | Shonfeld et al. | |
| 5,891,105 A | 4/1999 | Mahurkar | |
| 5,913,846 A | 6/1999 | Szabo | |
| 5,989,226 A | 11/1999 | Hymanson | |
| 5,997,513 A | 12/1999 | Smith et al. | |
| 6,013,059 A | 1/2000 | Jacobs | |
| 6,033,386 A | 3/2000 | Novacek et al. | |
| 6,086,566 A | 7/2000 | Arnissolle | |
| 6,159,184 A | 12/2000 | Perez et al. | |
| 6,171,284 B1 | 1/2001 | Kao et al. | |
| 6,186,980 B1 | 2/2001 | Brunel | |
| 6,296,625 B1 | 10/2001 | Vetter et al. | |
| 6,319,233 B1 | 11/2001 | Jansen et al. | |
| 6,319,234 B1 | 11/2001 | Restelli et al. | |
| 6,344,032 B1 | 2/2002 | Perez et al. | |
| 6,416,323 B1 | 7/2002 | Grenfell et al. | |
| 6,419,658 B1 | 7/2002 | Restelli et al. | |
| 6,475,194 B2 | 11/2002 | Domici, Jr. et al. | |
| 6,547,764 B2 | 4/2003 | Larsen et al. | |
| 6,565,540 B1 | 5/2003 | Perouse et al. | |
| 6,569,115 B1 | 5/2003 | Barker et al. | |
| 6,585,702 B1 | 7/2003 | Brunel | |
| 6,613,022 B1 | 9/2003 | Doyle | |
| 6,623,459 B1 | 9/2003 | Doyle | |
| 6,685,676 B2 | 2/2004 | Jansen et al. | |
| 6,719,730 B2 | 4/2004 | Jansen et al. | |
| 6,918,889 B1 | 7/2005 | Brunel | |
| 6,949,086 B2 | 9/2005 | Ferguson et al. | |
| 6,966,898 B1 | 11/2005 | Pouget et al. | |
| 6,997,901 B2 | 2/2006 | Popovsky | |
| 7,029,461 B2 | 4/2006 | Ferguson et al. | |
| 7,097,636 B2 | 8/2006 | Pessin | |
| 7,144,389 B2 | 12/2006 | Ferguson et al. | |
| 7,300,421 B1 | 11/2007 | Lowry et al. | |
| 7,429,256 B2 | 9/2008 | Chevallier et al. | |
| 7,582,073 B2 | 9/2009 | Barrelle et al. | |
| 7,678,086 B2 | 3/2010 | Chevallier | |
| 7,699,814 B2 | 4/2010 | Lande | |
| 7,824,379 B2 | 11/2010 | Doyle | |
| 7,875,006 B2 | 1/2011 | Pessin | |
| 7,938,808 B2 | 5/2011 | Pessin | |
| 8,118,787 B2 | 2/2012 | Chevallier et al. | |
| 8,192,407 B2 | 6/2012 | Pessin | |
| 2001/0031949 A1 | 10/2001 | Asbaghi | |
| 2001/0039401 A1 | 11/2001 | Ferguson et al. | |
| 2002/0002354 A1 | 1/2002 | Vetter et al. | |
| 2002/0045864 A1 | 4/2002 | Perez et al. | |
| 2002/0068921 A1 | 6/2002 | McWethy et al. | |
| 2002/0156426 A1 | 10/2002 | Gagnieux et al. | |
| 2002/0161337 A1 | 10/2002 | Shaw et al. | |
| 2002/0193746 A1 * | 12/2002 | Chevallier | 604/197 |
| 2003/0050607 A1 | 3/2003 | Gagnieux et al. | |
| 2003/0229314 A1 | 12/2003 | McWethy et al. | |
| 2004/0015137 A1 | 1/2004 | Hohlfelder et al. | |
| 2004/0144668 A1 | 7/2004 | Marshall et al. | |
| 2004/0193120 A1 | 9/2004 | Ferguson et al. | |
| 2004/0236283 A1 | 11/2004 | Tang | |
| 2004/0267206 A1 | 12/2004 | Rimlinger et al. | |
| 2005/0020985 A1 | 1/2005 | Doyle | |
| 2005/0080383 A1 | 4/2005 | Woehr | |
| 2005/0119623 A1 | 6/2005 | Pessin | |
| 2005/0148933 A1 | 7/2005 | Raven et al. | |
| 2005/0148943 A1 | 7/2005 | Chevalier | |
| 2005/0165353 A1 | 7/2005 | Pessin | |
| 2006/0184133 A1 | 8/2006 | Pessin | |
| 2006/0200077 A1 | 9/2006 | Righi et al. | |
| 2006/0264887 A1 | 11/2006 | Lande | |
| 2007/0088287 A1 | 4/2007 | Chevallier | |
| 2007/0179441 A1 | 8/2007 | Chevallier | |
| 2007/0239117 A1 * | 10/2007 | Chelak et al. | 604/198 |
| 2008/0021409 A1 | 1/2008 | Pessin | |
| 2008/0208140 A1 | 8/2008 | Barrelle | |
| 2008/0294120 A1 | 11/2008 | Chevallier et al. | |
| 2008/0312603 A1 | 12/2008 | Chevallier et al. | |
| 2009/0105661 A1 | 4/2009 | Chevallier et al. | |
| 2012/0022465 A1 | 1/2012 | Stamp et al. | |
| 2012/0095408 A1 | 4/2012 | Eaton et al. | |
| 2014/0121605 A1 | 5/2014 | Feret et al. | |

FOREIGN PATENT DOCUMENTS

| | | |
|---|---|---|
| EP | 1 066 848 A2 | 1/2001 |
| EP | 1474194 A1 | 11/2004 |
| EP | 1532997 A1 | 5/2005 |
| EP | 1235603 B1 | 5/2006 |
| FR | 2653667 A1 | 5/1991 |
| FR | 2762790 A1 | 11/1998 |
| FR | 2794650 A1 | 12/2000 |
| FR | 2807665 A1 | 10/2001 |
| FR | 2830764 A1 | 4/2003 |
| FR | 2830765 A1 | 4/2003 |
| FR | 2835753 A1 | 8/2003 |
| FR | 2837107 A1 | 9/2003 |
| FR | 2860162 A1 | 4/2005 |
| FR | 2861598 A1 | 5/2005 |
| FR | 2922455 A1 | 4/2009 |
| JP | H05-500621 T | 2/1993 |
| JP | H05-010324 A | 1/1996 |
| JP | H09-502893 T | 3/1997 |
| JP | 2843677 B2 | 1/1999 |
| JP | H11-319090 A | 11/1999 |
| JP | 2003-501218 A | 1/2003 |
| JP | 2003-511106 A | 3/2003 |
| JP | 2004-528075 T | 9/2004 |
| JP | 2005-516741 T | 6/2005 |
| JP | 2006-505340 A | 2/2006 |
| WO | 9426334 A1 | 11/1994 |
| WO | 9835714 A1 | 8/1998 |
| WO | 99 17823 A1 | 4/1999 |
| WO | 0124856 A1 | 4/2001 |
| WO | 0130427 A1 | 5/2001 |
| WO | 0137898 A2 | 5/2001 |
| WO | 0141841 A2 | 6/2001 |
| WO | 0185239 A2 | 11/2001 |
| WO | 02072182 A1 | 9/2002 |

(56) References Cited

FOREIGN PATENT DOCUMENTS

| WO | 02089878 | A1 | 11/2002 |
|---|---|---|---|
| WO | 03068298 | A1 | 8/2003 |
| WO | 03/077977 | A2 | 9/2003 |
| WO | 2004043524 | A1 | 5/2004 |
| WO | 2004087242 | A1 | 10/2004 |
| WO | 2005039678 | A2 | 5/2005 |
| WO | 2006/027445 | A1 | 3/2006 |

OTHER PUBLICATIONS

Office Action issued Mar. 22, 2011 in U.S. Appl. No. 12/738,422.
Office Action issued Aug. 18, 2011 in U.S. Appl. No. 12/738,422.
Office Action issued Jul. 1, 2009 in U.S. Appl. No. 12/254,266 by Chevallier.
Office Action issued Feb. 4, 2020 in U.S. Appl. No. 12/254,266 by Chevallier.
Office Action issued Nov. 3, 2011 in U.S. Appl. No. 12/254,266 by Chevallier.
Office Action issued Apr. 23, 2012 in U.S. Appl. No. 12/254,266 by Chevallier.
Office Action issued May 10, 2013 in U.S. Appl. No. 12/254,266 by Chevallier.
Office Action issued Oct. 10, 2013 in U.S. Appl. No. 12/254,266 by Chevallier.
Office Action issued Sep. 28, 2010 in JP Application No. 2007-528913.
Search Report issued Feb. 22, 2005 in EP Application No. 04 29 2750.
Action issued Nov. 28, 2006 in EP Application No. 04 292 750.
Office Action issued Mar. 11, 2008 in EP Application No. 04 292 750.
Office Action issued Sep. 11, 2009 in EP Application No. 05 792 448.
Int'l Preliminary Report on Patentability issued Dec. 12, 2013 in Int'l Application No. PCT/US2012/039385.
Office Action issued Oct. 24, 2013 in U.S. Appl. No. 11/861,567 by Pessin.
Japanese Office Action mailed Mar. 16, 2010 in JP Appln No. 2006-537346.
Int'l Search Report and Written Opinion issued Dec. 22, 2011 in Int'l Application PCT/US2011/031053.
Office Action issued Mar. 28, 2007 in U.S. Appl. No. 10/550,524.
Int'l Search Report issued Sep. 22, 2004 in Int'l Application No. PCT/FR2004/000755.
Office Action issued Apr. 17, 2009 in U.S. Appl. No. 11/861,567.
Office Action issued Jan. 13, 2010 in U.S. Appl. No. 11/861,567.
Office Action issued Sep. 1, 2009 in JP Application No. 2006-505752.
Office Action issued Jun. 8, 2010 in JP Application No. 2006-505752.
Office Action issued Dec. 7, 2010 in JP Application No. 2006-505752.
Search Report Issued Jul. 9, 2009 in EP Application No. 08 166 632.3.
Search Report Issued Jun. 13, 2008 in FR Application No. 0758496.
Japanese Office Action mailed Feb. 2, 2010 in Japanese Appln No. 2006-536115.
Office Action Issued Oct. 2, 2008 in U.S. Appl. No. 10/576,938.
Office Action Issued Jul. 21, 2009 in U.S. Appl. No. 10/576,938.
Preliminary Search Report Issued Jun. 21, 2004 in FR Application No. 0312327.
International Search Report and Written Opinion mailed Jun. 6, 2005 in Int'l Application No. PCT/FR2004/002654.
Office Action Issued Dec. 22, 2008 in EP Application No. 04817285.2.
Int'l Preliminary Report on Patentability Issued Jul. 27, 2006 in Int'l Application No. PCT/FR2004/002654.
Office Action dated Mar. 9, 2010 in U.S. Appl. No. 10/576,938.
U.S. Appl. No. 14/009,814 by Chevallier, filed Oct. 4, 2013.
Int'l Preliminary Report on Patentability issued Oct. 8, 2013 in Int'l Application No. PCT/US2011/031053.
Office Action issued Dec. 18, 2006 in U.S. Appl. No. 10/507,913 by Pessin.
Office Action issued Sep. 7, 2007 in U.S. Appl. No. 10/507,913 by Pessin.
Office Action issued Dec. 17, 2008 in U.S. Appl. No. 10/507,913 by Pessin.
Office Action issued Oct. 8, 2009 in U.S. Appl. No. 10/507,913 by Pessin.
Office Action issued Apr. 23, 2009 in EP Application No. 04 818 444.4.
Office Action issued Nov. 23, 2010 in EP Application No. 04 818 444.4.
Office Action issued Apr. 17, 2013 in EP Application No. 04 818 444.4.
Search Report and English translation of Written Opinion Opinioon issued Jul. 9, 2009 in EP Application No. 08 166 632.3.
Office Action issued Apr. 21, 2005 in U.S. Appl. No. 10/995,035 by Pessin.
Office Action issued Oct. 5, 2005 in U.S. Appl. No. 10/995,035 by Pessin.
Office Action issued Sep. 28, 2010 in JP Application No. 2007-528915.
Office Action issued Sep. 6, 2011 in JP Application No. 2007-528915.
Int'l Search Report issued Jan. 3, 2006 in Int'l Application No. PCT/FR2005/001983.
Int'l Preliminary Report on Patentability issued Feb. 28, 2007 in Int'l Application No. PCT/FR2005/01983.
Int'l Search Report issued Jan. 25, 2006 in Int'l Application No. PCT/FR2005/001926.
Int'l Preliminary Report on Patentability issued Feb. 28, 2007 in Int'l Application No. PCT/FR2005/001926.
Office Action issued May 13, 2009 in U.S. Appl. No. 11/574,333 by Pessin.
Office Action issued Sep. 10, 2008 in U.S. Appl. No. 11/574,333 by Pessin.
Office Action issued Dec. 13, 2007 in U.S. Appl. No. 11/574,333 by Pessin.
Office Action issued Aug. 20, 2010 in U.S. Appl. No. 11/574,176 by Pessin.
Int'l Preliminary Report on Patentability issued Feb. 21, 2006 in Int'l Application No. PCT/FR2004/000755.
Search Report issued Mar. 4, 2004 in FR Application No. 0312642.
Int'l Search Report issued Apr. 4, 2005 in Int'l Application No. PCT/FR2004/002597.
Office Action issued Mar. 11, 2009 in U.S. Appl. No. 10/577,380 by Chevallier.
Office Action issued Feb. 16, 2012 in CN Application No. 200880112413.1.
Int'l Search Report and Written Opinion issued May 11, 2009 in Int'l Application No. PCT/FR2008/051907.
Search Report issued Jun. 17, 2008 in FR Application No. 0758497; Written Opinion.
Office Action issued Dec. 23, 2011 in CN Application No. 200880112730.3
Int'l Search Report issued Dec. 12, 2012 in Int'l Application PCT/US2012/039385.
Office Action issued Jun. 16, 2014 in U.S. Appl. No. 10/576,938 by Chevalier.
Int'l Search Report issued May 11, 2009 in Int'l Application No. PCT/FR2008/051908; Written Opinion.
Office Action issued Sep. 14, 2010 in Japanese Appl Ser No. 2006-536115.
Int'l Search Report issued Sep. 11, 2003 in Int'l Application No. PCT/FR2003/000722.
Search Report and Written Opinion issued Jun. 13, 2008 in FR Application No. 0758495.
Int'l Preliminary Report on Patentability issued Oct. 17, 2013 in Int'l Application No. PCT/US2011/031053.
Int'l Preliminary Report on Patentability issued Jun. 1, 2010 in Int'l Application No. PCT/FR2008/051908.
Search Report issued Jun. 24, 2004 in FR Application No. 0312327.
Office Action issued Jul. 18, 2014 in U.S. Appl. No. 14/009,814 by Chevalier.
Office Action issued Jan. 8, 2015 in U.S. Appl. No. 10/576,938 by Chevalier.
Office Action issued Aug. 28, 2015 in U.S. Appl. No. 10/576,938 by Chevallier.

* cited by examiner

SYRINGE DEVICE COMPRISING A SYRINGE BODY AND A BEARING SLEEVE

CROSS-REFERENCE TO RELATED APPLICATIONS

This application is a Section 371 of International Application No. PCT/FR2008/051908, filed Oct. 22, 2008, which was published in the French language on May 7, 2009, under International Publication No. WO 2009/056735 A2, and the disclosure of which is incorporated herein by reference.

BACKGROUND OF THE INVENTION

The invention relates to a device comprising a syringe body having an axial direction and a bearing sleeve inside which the body is arranged. The sleeve has at least one holding lug co-operating with the syringe body, at a proximal end of the latter, in order to hold the body in relation to the sleeve.

For the scope of the present invention, the term "syringe" includes both a syringe with a flange at its proximal end and an object of the type of carpule or ampoule, the type used in the cosmetics or pharmaceutical field, whether it is equipped with such a flange or not. Thus, for the scope of the invention, the "syringe body" presents a general cylindrical shape and may contain inside a liquid, gaseous, or pasty fluid, which can be expelled through its distal extremity, for example under the action of a piston, disposed inside the body and pushed toward the distal end.

The bearing sleeve can simply serve to support the syringe body inside. It can also be part of a safety support device for the syringe, for example the type described in EP 1 235 603 and EP 1 474 194.

In these known devices, the syringe body is kept inside the bearing sleeve, generally without being able to move axially in relation to it. The holding lug or lugs of the bearing sleeve permit in fact an efficient hold of the syringe body in relation to the sleeve, in an axial direction, due to their co-operation with the proximal end of the syringe body. Nevertheless, in the known devices, the syringe body can turn in relation to the bearing sleeve, with a rotation around the axis defining the axial direction.

In certain cases, this rotational freedom can be tolerated as it does not influence the operation of the device or, in particular, the preparatory operations for the injection of the product contained in the syringe body. In other cases, it is actually necessary to be able to secure the syringe body rotating in relation to the sleeve. In fact, it may be that the syringe body is such that an injection needle or an end piece must be attached to the distal end of the syringe body by rotation, in particular by tightening. The syringe body may also initially include an injection needle or an end piece protected by a cap protector, which must be removed through a twisting movement in order to allow for an injection.

Thus, it helps to have the syringe body wedged in rotation to allow either the mounting of the needle or the separation of the protection sleeve, in relation to the syringe body.

BRIEF SUMMARY OF THE INVENTION

In general, the invention concerns a device of the aforementioned type and which purposely allows for wedging through rotation of the syringe body in relation to the bearing sleeve in a simple way, whatever the reasons why this wedging through rotation is needed.

This purpose is attained due to the fact that the proximal end of the syringe body is fixed to a wedging surface having radial crenulations forming dips and bumps and the holding lug has been inserted into a dip in order to prevent a relative rotation of the syringe body and of the bearing sleeve perpendicularly to the axial direction.

Thus, due to this invention, the holding lug of the protection sleeve serves not only to acquire the axial hold mentioned in the preamble, but also to obtain the wedging through rotation. Thus, the manufacturing of the entire invention device remains extremely simple, just like its assembly.

Furthermore, the holding lug is elastic in general and can be removed flexibly to allow the insertion of the syringe body and the wedging surface connected to the body in the bearing sleeve and returns immediately to its holding position. Consequently, after assembling the device, the holding lug co-operates with the proximal end of the syringe body and, if this lug is not immediately co-operating with a dip from the wedging surface blocking the relative rotation of the syringe body and the sleeve, it is enough to accomplish voluntarily such a relative rotation until the lug is located in a dip on the wedging surface, thus being able to hold in relation to the latter. Consequently, the assembly is extremely simple and does not require any pre-adjustments meant to bring the holding lug and the wedging depth in range before the assembly.

Moreover, the dips and bumps are easy to manufacture and allow the effortless wedging positioning as, in order to accomplish the wedging, it is enough to have at a minimum one holding lug inserted in one of the dips.

In conformity with a first application, the syringe body presents a flange placed at the proximal end of the said body, the wedging surface being placed at the proximal end of the flange.

In this situation, the wedging surface can be created directly on the flange of the syringe body integral with the body.

This option allows for angular wedging without increasing the number of component parts of the device. It is particularly useful when the syringe body is made out of plastic, by molding, but this obviously does not exclude the usage of other materials, for example, glass.

According to an alternative, the device includes one wedging part in relation to the proximal end of the syringe body so as to create the wedging surface.

In this case, the syringe body used in the device of the invention may be of a very classic type and it is enough to relate the wedging part to its proximal end in order to allow this body to accomplish an angular wedging. According to this alternative, the syringe body may have a flange of the aforementioned type, or conversely may not have a flange.

Under this alternative, the wedging surface is preferably formed on a part of the flange of the wedging part, in radial projection from the cylindrical wall of the syringe body. When the syringe body includes a flange, the flange part of the wedging part can be placed on the syringe body flange. The flange part of the wedging part may be more or less rigid, its axial rigidity being ensured by the syringe body flange on which it rests.

In this case, the flange part of the wedging part may be positioned against the surface of the flange formed at the proximal end of the syringe body, without increasing noticeably the dimensions of the ensemble created by the syringe body and the wedging part, in relation to the initial dimensions of the syringe body. This allows creating the device of the invention with minimal space requirements.

When the syringe is of a carpule or ampule type, without a flange, the flange part of the wedging part is preferentially chosen to be rigid axially in order to avoid bending under the efforts exerted on it by the holding lug or lugs.

Advantageously, the device includes, among others, a protective sleeve, the protective sleeve and the support sleeve being able to slide in relation with the other between a standby setting, in which a needle found at the distal end of the syringe body may protrude in relation with the protective sleeve and a security setting, in which it is possible that the needle is surrounded by the protective sleeve.

In this situation, the invention is equipped with a safety device.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 1A shows an option for the distal end part of the syringe body;

DETAILED DESCRIPTION OF THE INVENTION

Figure 1:
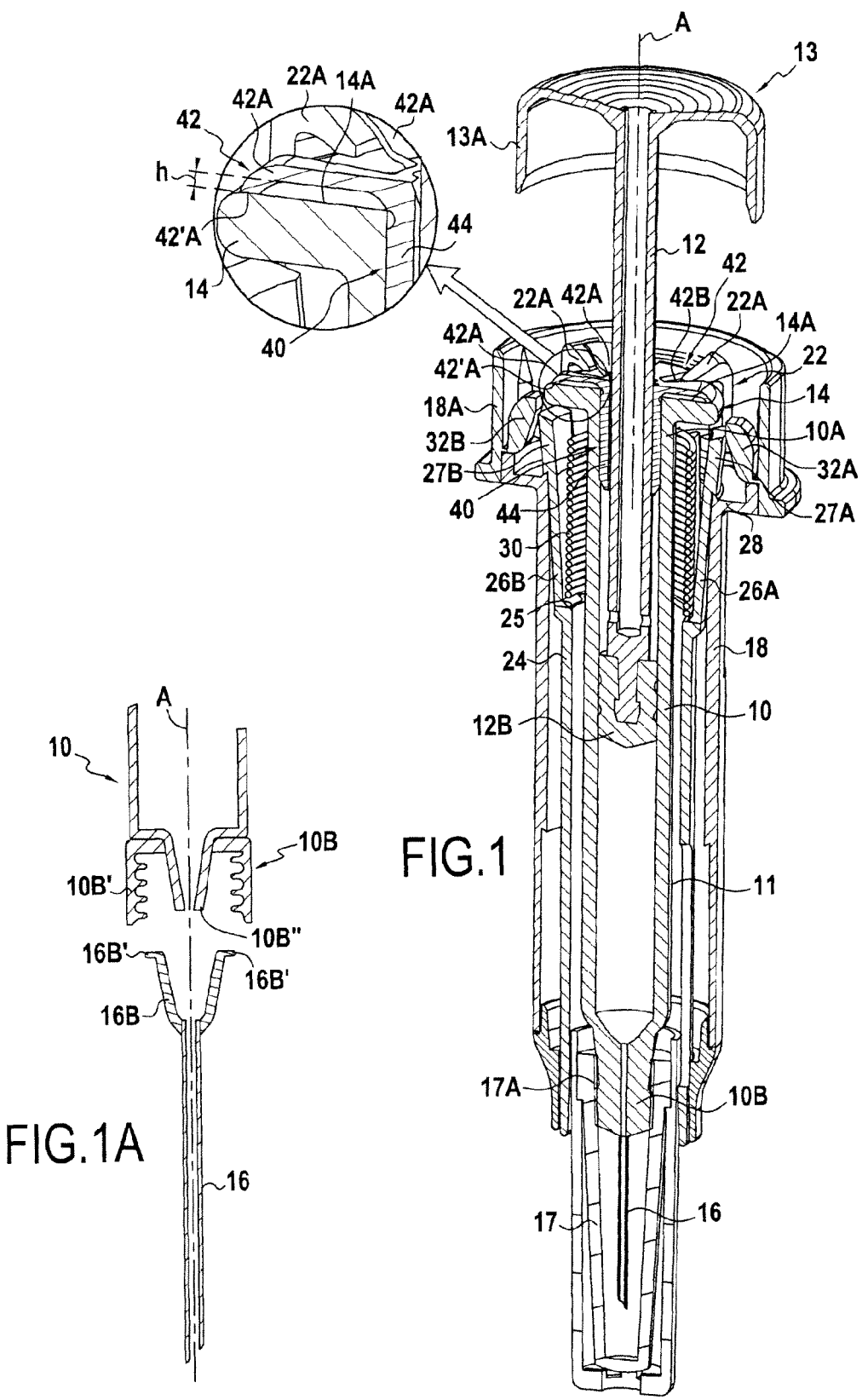
FIG. 1 shows a perspective view of a device to conform to the invention according to a first embodiment, having a cross-section along a diametral axial plane.
Figure 2:
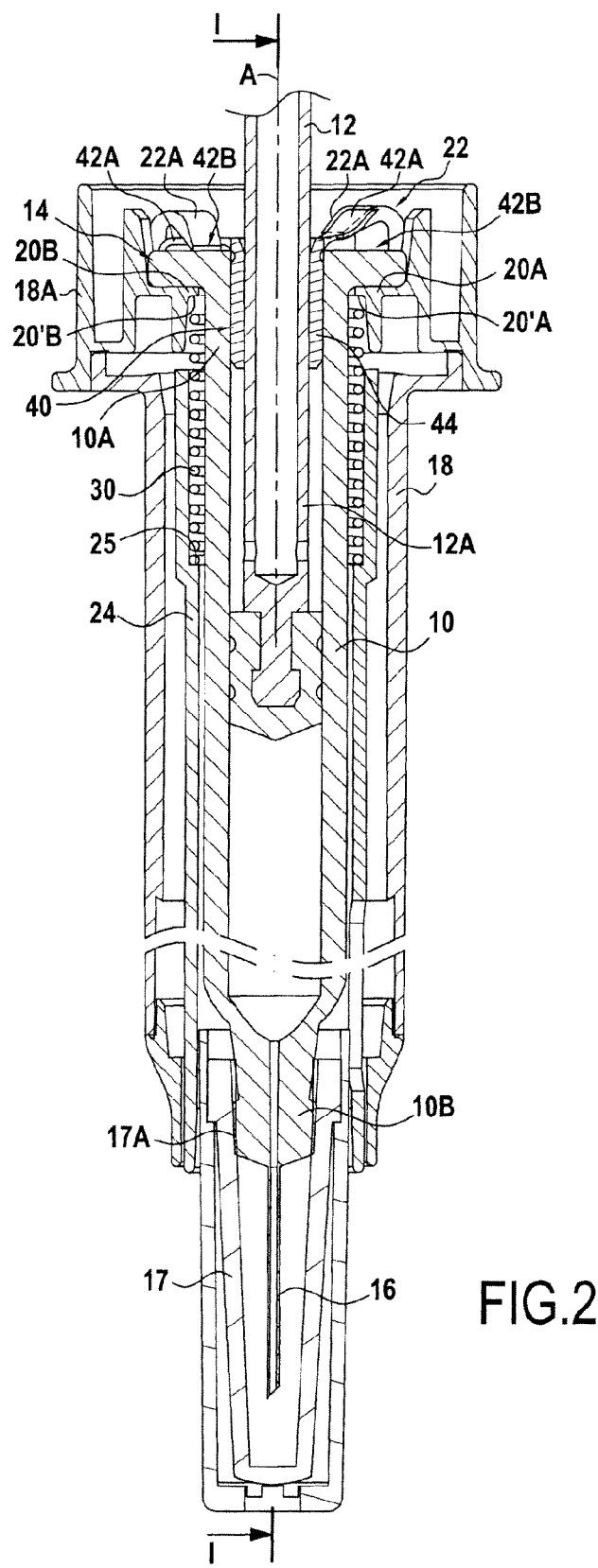
FIG. 2 is a cross-sectional, elevational view of FIG. 1.

The device shown in FIGS. 1 and 2 include a syringe body 10 with an axial direction according to axis A in which the piston 12 can slide along this axial direction between a position of beginning an injection and of ending an injection. The piston is inserted into the syringe body starting from the proximal end 10A of the latter, this proximal end having a flange 14 stretching radially. At its distal end 10B, the syringe body has an injection needle 16.

For the scope of the present text, the proximal end is the one closest to the fingers of the user handling the device for an injection, while the distal end is the opposite end, through which the fluid contained in the syringe body is ejected.

The syringe body is held in a bearing sleeve 18. At its proximal end 18A, the bearing sleeve 18 presents shoulder stops 20A and 20B (see FIG. 2), as well as holding lugs 22. It can be seen that the flange 14 is retained between the shoulders 20A and 20B on which it rests and the holding lugs 22. Thus, the syringe body is wedged axially in relation to the bearing sleeve 18. In this particular case are provided four holding lugs 22, but it is obvious that their number can be different.

The device presented in FIGS. 1 and 2 also include a protection sleeve 24, able to slide in relation to the bearing sleeve 18 between a standby setting and a protection setting. In FIG. 1 it can be seen that the protection sleeve 24 is kept in its standby setting in relation with the bearing sleeve 18 through the longitudinal lugs 26A and 26B, whose proximal ends, respectively 27A and 27B, are shaped as hooks locking on a ring shaped shoulder 28 of the bearing sleeve 18. A spring 30 is introduced between the inferior surface, respectively 20'A and 20'B of the shoulders 20A and 20B and an internal shoulder ring 25 of the protection sleeve. The device also includes tabs, respectively 32A and 32B, which are connected to the proximal end 18A of the protection sleeve 18. The head 13 of the piston 12 includes an axial skirt 13A.

It is understood that, at the end of the injection, the axial skirt 13A exerts pressure on the tabs 32A and 32B, bending them toward axis A, which also leads to bending the lugs 26A and 26B in the same direction, so that their hook shaped proximal ends 27A and 27B are released from the shoulder 28. Due to the return force exerted by the spring 30, the protection sleeve 24 can then slide toward the distal end relative to the bearing sleeve 18, in order to surround the needle and thus protect the latter.

For what has been described, the device presented in FIG. 1 is in conformity to the one presented in EP 1 474 194 and thus will not be described in detail anymore.

This is only an exemplary embodiment since, as noted above, it can be expected that the device includes a bearing sleeve as the sleeve, without a protection sleeve.

In addition, a different embodiment between the protection and the support sleeves can be foreseen allowing, for example, at the end of the injection, a resetting of the ensemble made of the syringe body and the bearing sleeve inside the protection sleeve.

Also, the device of the invention may be used in all types of systems including a syringe body retained inside a bearing sleeve by its axial flange and by the sleeve's holding lugs.

On FIGS. 1 and 2 it can be seen that the needle 16 is surrounded by a protection cap 17 held in a non-movable position in relation to the distal end 10B of the syringe body. In this particular case, the protection cap is held by tightening to the external rim of the syringe body, as indicated in 17A in FIGS. 1 and 2. Its unscrewing requires the syringe body to be fixed in rotation in relation to the bearing sleeve, held by the user.

In FIG. 1A, the distal end 10B of the syringe body 10 is able to co-operate by tightening with the needle. The end 10B of the syringe body includes a tightening ring 10B' which surrounds its end piece 10B" with a space. This ring is threaded on its internal rim turned toward the A axis. The needle 16 is attached, at its proximal end, to a connector 16B which can be placed around the end piece 10B" and screwed in, by its studs 16B', in the ring 10B'. After the needle is mounted to the extremity of body 10 and in its place in the bearing sleeve, the body 10 must be prevented to rotate in relation to this sleeve held by the user.

According to the invention, the proximal end of the flange 14 (and precisely its proximal end surface 14A oriented transversally on the A axis) presents a wedging surface preventing the rotation of the syringe body in relation to the bearing sleeve. In this particular case, according to the embodiment of FIGS. 1 and 2, this wedging surface is created through a wedging part 40 relating to the proximal end 10A of the syringe body 10.

The wedging part 40 consists of a flange part 42 (see also FIGS. 3 and 4) which stretches radially and which is placed on the flange 14 of the syringe body, more exactly being placed against the proximal end surface 14A. The flange part 42 has ribs 42A which are significantly oriented in a radial direction and create bumps of the wedging surface, these bumps being separated ones from the others by dips 42B which form dents on the wedging surface. In this particular case the ribs are separated by indentations, the dips being perpendicular on the axial direction. It can be easily imagined this dips simply correspond to areas of the flange 42 where the thickness of the flange, measured in the axial direction, would be less than the thickness in the area of the bumps.

The wedging part 40 also includes an axial tubular part 44 which, as it can be seen on FIGS. 1 and 2, is inserted in the syringe body 10, starting from the proximal end 10A of the latter. The width L of the dips 42B, measured in the circumferential direction of the flange 42, corresponds to the size of the active holding parts of the holding lug 22, measured also in the circumferential direction around axis A. In this particular case, it can be seen that these active holding parts are formed by the attachment heads 22A of the holding lugs 22, so the size will decrease when getting closer to the A axis, meaning when getting closer to their free ends. These attachment heads are formed by the ends of the lugs, which are curved toward the axis A, so as to extend sensibly transversally. Similarly, the size L of the dips 42B will decrease in the same direction.

The external diametral dimensions D of the tubular part 44 of the wedging part corresponding to the internal diametral dimensions of the syringe body 10, at the proximal end 10A of the latter, so as to allow a forced insertion of this tubular part 44 in the syringe body. In order to connect the wedging part 40 with the syringe body, it will be chosen to make the part 40 out of a material with a high coefficient of friction, for example a synthetic resin, an elastomer or a mixture of both. At the aforementioned forced insertion on the surfaces of the wedging part 40 and the syringe body 10 that are in contact, this material creates high friction forces which oppose a relative rotation between the syringe body and the wedging part. In this case, the contact can be obtained without any other specific means. Nevertheless, if needed, this binding may be accomplished via additional means, such as welding or gluing.

Figure 3:
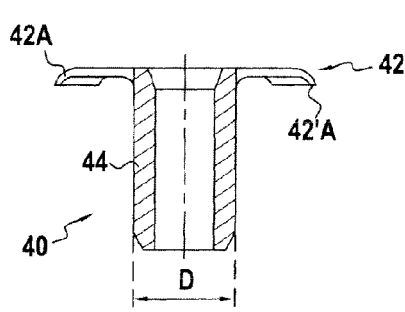
FIG. 3 shows a cross-sectional view of an example of the wedging part that may be part of the device of the invention.
Figure 4:
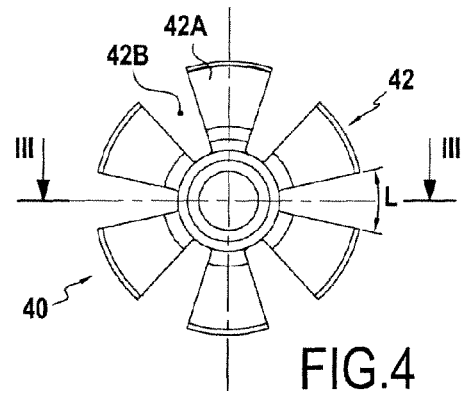
FIG. 4 is a plan view of the part from FIG. 3.
Figure 5:
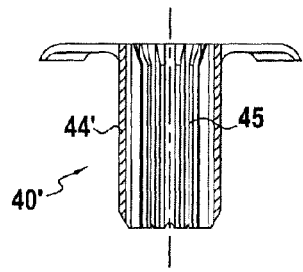
FIGS. 5 and 6 are respective views similar to FIGS. 3 and 4 for another embodiment of the wedging part.
Figure 6:
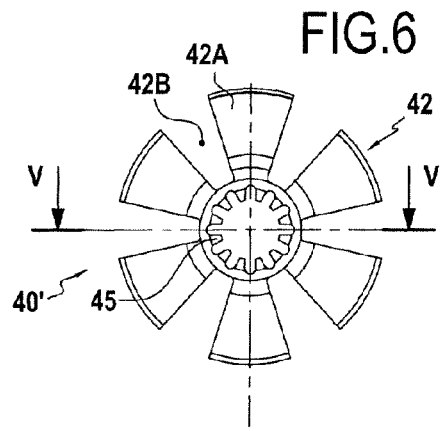

In the versions presented in FIGS. 3 and 4, the tubular part 44 is smooth. FIGS. 5 and 6 present a wedging part 40', similar to part 40 from FIGS. 3 and 4 and present in particular the same part of the flange 42, with the bumps 42A and the dips 42B. The part 40' differs from part 40 through its tubular part 44' which, on its internal rim (toward axis A), presents axial crenulations 45. These axial crenulations confer to the tubular part 44' radial direction elasticity. Thus, when the tubular part 44' is inserted in the proximal end 10A of the syringe body 10, the said tubular part 40' can be easily compressed radially by pressing together the protruding parts of the crenulations 45, thus decreasing its radial dimensions and favoring its insertion in the syringe body. Due to its natural elasticity, the tubular part 44' has a tendency of expanding in a radial direction that will wedge itself inside the syringe body.

In the two versions it can be seen that the free ends 42'A of the strips are slightly curved toward the distal end. As it can be seen in the enlarged part in FIG. 1, this allows maintaining the flat part of the strips 42A at a certain distance h from the proximal end surface 14A of the flange 14 of the syringe body. The bump effect is also increased by the presence of the strips.

In the right side of FIG. 1 it can be seen that the active holding part 22A of one of the holding lugs 22 is placed in a dip 42B in such a way that this holding lug is wedged angularly between the two strips delimitating the said dip.

On the other hand, in the left part of FIG. 1, the active part 22A of the wedging lug 22 is placed between the flange 14 and one of the strips 42A. In fact, it is necessary to chose only the number of slits and their angular distances corresponding exactly to the number of holding lugs and the angular distances of the holding active parts 22A of the latter. Due to the flexibility of the strips 42A and the holding lugs 22, it is perfectly possible to acquire the desired angular wedging from the moment one of the holding lugs is placed in a slit, even if this does not apply to the other holding lugs. In fact, it is enough if at least one of the elements consisting of the holding lug 22 and the flange part 42 is elastically flexible in order to allow an easy angular wedging positioning between the holding lug and a slit from the flange. This also permits, if several holding lugs are present, to obtain an efficient angular wedging even if only one holding lug is placed in a slit from the flange.

The tubular part 44 or 44' of the wedging part 40 or 40' causes occasionally a slight overpass inside the syringe body. The diametral dimensions of the piston rod 12 are chosen so that this rod may pass in the interior of the part 40 or 40' in order to connect to the plug 12B, already present inside the body before placing the part 40 or 40' at the proximal end of the syringe body. This overpass helps with stopping the extraction of the piston and of the plug 12B through the proximal end of the body 10, in order to save the product contained inside the body.

Figure 7:
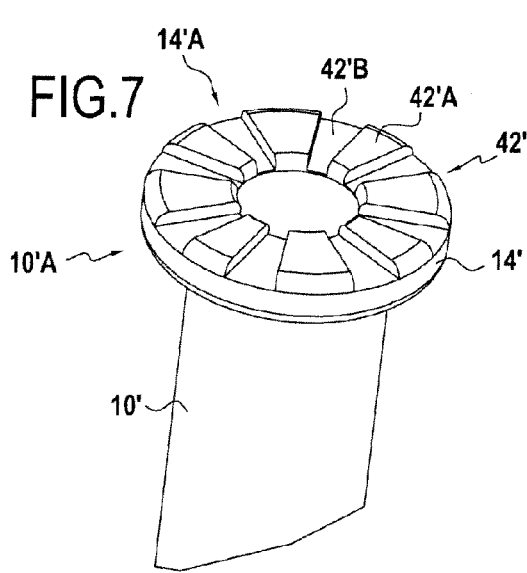
FIG. 7 shows a perspective view of a proximal extremity part of a syringe body in accordance with another embodiment of the invention device.

FIG. 7 illustrates the proximal end part 10'A of a syringe body 10' according to a second embodiment. In this case it can be seen that the wedging surface 42' is formed directly on the flange 14' of the syringe body. In fact, this flange presents, as part of its body, several protruding shapes 42'A delimitating between them dips 42'B. The configuration thus obtained is similar to the one obtained with the previous embodiment, once the wedging part is placed at the proximal end 10A of the syringe body 10. In fact, in the two situations, the alternation of dips and bumps creates radial crenulations able to allow at least an efficient angular hold of the holding lug 22.

Figure 8:
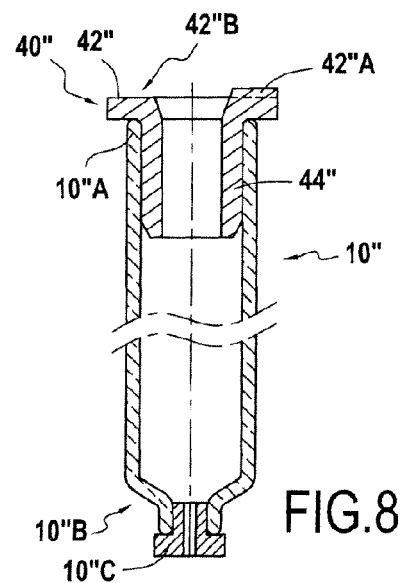
FIG. 8 shows a cross-sectional view of yet another embodiment of a device according to the invention.

FIG. 8 shows a syringe body 10" configured as a tubular carpule or ampoule, without a flange at its proximal end 10"A. The body has an end piece 10"C at its distal end 10"B, through which can be expelled the fluid contained inside the body. Additional parts (for example an injection adaptor) may be connected to this distal end, for example by clipping or tightening.

The wedging part 40", connected to the proximal end 10"A in an interdependent way to the syringe body, presents a flange part 42" as a radial protrusion in relation to the cylindrical wall of the body 10". The wedging bumps and dips are created by this part of the flange, just as with the flange 14' from FIG. 7.

The left part of the cross-sectional view goes through a dip 42"B, while the right part goes through a bump 42"A.

Even in the dips, the thickness of the flange part is chosen so as to give to the latter sufficient rigidity to handle the efforts exerted through the wedging lug or lugs without detrimentally effecting its wedging ability.

The tubular axial part 44" of the wedging part 40" can be similar to the axial parts 44 or 44' of the parts 40 and 40' described in reference with FIGS. 4 and 5.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:
1. A syringe device comprising:
 a syringe body (10; 10'; 10") having a central axis (A), a radially extending syringe flange (14, 14') at a proximal end of the syringe body and a needle proximate a distal end of the syringe body, a bearing sleeve (18) receiving the syringe body therein, the sleeve having at least one holding lug (22) co-operating with the syringe body at a proximal end (10A, 10'A, 10"A) of the syringe body, in order to hold the said body in relation to the sleeve, and an uneven wedging surface (42; 42'; 42") having alternating radially extending recessed portions (42B; 42'B; 42"B), formed by indentations extending in a direction of the central axis (A), and radially extending raised portions (42A; 42'A; 42"A), formed by ribs extending in the direction of the central axis (A), the recessed and raised portions alternating in a circumferential direction, wherein:

a distal surface of the wedging surface cooperatively abuts a proximal surface of the syringe flange and the at least one holding lug (22) is insertable in at least one of the recessed portions to prevent rotation of the syringe body (10; 10') relative to the bearing sleeve (18).

2. The device according to claim 1, further comprising a wedging part (40; 40'; 40") connectable to the proximal end (10A; 10"A) of the syringe body (10; 10") to form the wedging surface.

3. The device according to claim 2, wherein the wedging surface is created on a flange part (42; 42") of the wedging part (40; 40'; 40"), extending radially outwardly beyond a cylindrical wall (11) of the syringe body (10; 10").

4. The device according to the claim 3, wherein the flange part (42) of the wedging part (40; 40') has radially-extending strips (42A) forming the raised portions on the wedging surface, and the strips are separated by the indentations (42B) forming the recessed portions of the wedging surface.

5. The device according the claim 3, wherein at least one of the holding lug (22) and the flange part (42) is elastically flexible.

6. The device according to claim 2, wherein the wedging part (40; 40'; 40") has a tubular axial part (44; 44'; 44") sized and shaped to be inserted in the syringe body (10; 10"), starting from the proximal end (10A; 10"A) of the syringe body.

7. The device according to claim 6, wherein the tubular axial part (44'; 44") has crenulations (45).

8. The device according to claim 1, further comprising a protection sleeve (24), the protection sleeve and the bearing sleeve (18) being able to slide one in relation to the other between a standby setting where the needle (16) may protrude in relation to the protection sleeve (24) and a protection setting, where the needle (16) is able to be surrounded by the protection sleeve (24).

9. A syringe device comprising:

a syringe body (10; 10'; 10") having a central axis (A), a radially extending syringe flange (14, 14') at a proximal end of the syringe body and a needle proximate a distal end of the syringe body, a bearing sleeve (18) receiving the syringe body therein, the sleeve having at least one holding lug 22 co-operating with the syringe body at a proximal end (10A, 10'A, 10"A) of the syringe body, in order to hold the said body in relation to the sleeve, and an uneven wedging surface (42; 42'; 42") having alternating radially extending recessed portions (42B; 42'B; 42"B), formed by indentations extending in a direction of the central axis (A), and radially extending raised portions (42A; 42'A; 42"A), formed by ribs extending in the direction of the central axis (A), the recessed and raised portions alternating in a circumferential direction, wherein the wedging surface (42') is formed integrally with the flange (14') of the syringe body (10'), and the at least one holding lug (22) is insertable in at least one of the recessed portions to prevent rotation of the syringe body (10; 10') relative to the bearing sleeve (18).

10. A syringe device comprising:

a syringe body having a central axis (A), a radially extending syringe flange at a proximal end of the syringe body and a needle proximate a distal end of the syringe body, a wedging part having a proximal flange part defining alternating radially extending recessed portions, formed by indentations extending in a direction of the central axis (A), and radially extending raised portions, formed by ribs extending in the direction of the central axis (A), that alternate in a circumferential direction, the wedging part cooperating with the syringe body such that a distal surface of the flange part cooperatively abuts a proximal surface of the syringe flange, and a bearing sleeve housing the syringe body, the bearing sleeve having at least one holding lug inserted on at least one of the radially extending recessed portions and cooperating with the syringe body at a proximal end of the syringe body to hold the syringe body in relation to the bearing sleeve.

11. The syringe device of claim 10, wherein the wedging part is retained between the bearing sleeve and the holding lug.

\* \* \* \* \*